United States Patent
Hara et al.

(10) Patent No.: US 10,206,857 B2
(45) Date of Patent: Feb. 19, 2019

(54) DENTAL PRIMER COMPOSITION HAVING ADHESIVE PROPERTY TO RESIN CURED MATERIAL

(71) Applicant: SHOFU INC., Kyoto (JP)

(72) Inventors: Daisuke Hara, Kyoto (JP); Naoya Kitada, Kyoto (JP)

(73) Assignee: SHOFU INC., Kyoto (JP)

( * ) Notice: Subject to any disclaimer, the term of this patent is extended or adjusted under 35 U.S.C. 154(b) by 0 days.

(21) Appl. No.: 15/264,968

(22) Filed: Sep. 14, 2016

(65) Prior Publication Data

US 2017/0071831 A1 Mar. 16, 2017

(30) Foreign Application Priority Data

Sep. 16, 2015 (JP) .................. 2015-183164
Sep. 6, 2016 (JP) .................. 2016-173865

(51) Int. Cl.
*A61K 6/083* (2006.01)
*A61K 6/00* (2006.01)
*C09J 4/00* (2006.01)

(52) U.S. Cl.
CPC .............. *A61K 6/0029* (2013.01); *A61K 6/00* (2013.01); *A61K 6/0023* (2013.01); *C09J 4/00* (2013.01); *A61K 6/083* (2013.01)

(58) Field of Classification Search
CPC .................................................... A61K 6/083
See application file for complete search history.

(56) References Cited

U.S. PATENT DOCUMENTS

| 5,295,824 | A | 3/1994 | Wong |
| 5,558,516 | A | 9/1996 | Horn et al. |
| 5,770,638 | A | 6/1998 | Ueno et al. |
| 6,288,138 | B1 * | 9/2001 | Yamamoto ........... A61K 6/0023 522/17 |
| 2010/0069524 | A1 | 3/2010 | Tanaka et al. |
| 2010/0292359 | A1 * | 11/2010 | Yamamoto ........... A61K 6/0017 522/78 |
| 2012/0202913 | A1 * | 8/2012 | Kawana ............... A61K 6/0023 522/84 |

FOREIGN PATENT DOCUMENTS

| EP | 0 142 172 | 5/1985 |
| EP | 0 383 595 | 8/1990 |
| JP | 07-277913 | 10/1995 |
| JP | 8-277207 | 10/1996 |
| JP | 10-109916 | 4/1998 |
| JP | 2006-045094 | 2/2006 |
| JP | 2008-001624 | 1/2008 |
| JP | 2015-020977 | 2/2015 |
| WO | 2008/053990 | 5/2008 |
| WO | 2014/139932 | 9/2014 |

OTHER PUBLICATIONS

Database WPI, Week 200136, Thomson Scientific, London, GB; AN 2001-338608, XP002764276, & JP 2001 089693 A (Kuraray Co Ltd), Apr. 3, 2001 (Apr. 3, 2001), * abstract *.
Extended European Search Report dated Nov. 25, 2016 in corresponding European Patent Application No. 16188634.6.

* cited by examiner

*Primary Examiner* — Michael F Pepitone
(74) *Attorney, Agent, or Firm* — Wenderoth, Lind & Ponack, L.L.P.

(57) ABSTRACT

A primer composition for a resin cured material according to the present disclosure comprising (A) a polymerizable monomer having a solubility parameter (an SP value) in the range of from 7.0 to 10.0, (B) a volatile organic solvent, (C) a polymerization catalyst and/or a polymerization accelerator, and (D) a polymerizable monomer having at least two polymerizable group.

7 Claims, No Drawings

DENTAL PRIMER COMPOSITION HAVING ADHESIVE PROPERTY TO RESIN CURED MATERIAL

BACKGROUND OF THE INVENTION

Field of the Invention

The present disclosure relates to a dental primer composition used for exhibiting an adhesive property to a crown hard resin and a resin cured material for CAD/CAM, more specifically, to a dental primer composition for a prosthesis article having an excellent initial adhesive property and an excellent adhesive durability.

Description of the Related Art

When a size of a lost part is relatively large, a general method of restoration of a teeth having the lost part by caries etc. is a prosthesis restoration method. In this method, a prosthesis article adapting a shape of a restoration part, such as an inlay, an onlay, and a crown is previously prepared in outside of an oral cavity, and this prosthesis article is adhered by a dental adhesive agent. Especially, from the view point of aestheticity and a metal allergy, instead of a conventional metallic prosthesis article, a prosthesis article consisting of a crown hard resin and a resin cured material for CAD/CAM prepared by thermal polymerizing and/or photo polymerizing of a composite material including a methacrylate-base polymerizable monomer and an inorganic filler is mainly used.

Some cured resin materials have material strength approximate to teeth by thermal polymerizing and/or photo polymerizing. Especially, a cured resin material prepared by a high degree of thermal polymerizing, such as cured resin material for CAD/CAM, has very high material strength, and therefore can be applied to molar tooth which is applied with occlusal pressure. For adhesion of these resin cured materials, a primer containing a silane coupling agent which may chemically bond to an inorganic filler contained in the resin cured material is widely used (See, Japanese Unexamined Patent Application Publication No. H07-277913 (JPH7-277913 A), Japanese Unexamined Patent Application Publication No. 2008-1624 (JP2008-1624 A), Japanese Unexamined Patent Application Publication (Translation of PCT Application) No. 2008-053990 (JP2008-053990 A)). A silanol group is formed by hydrolysis of the silane coupling agent, and exhibits an adhesive property by condensation reaction with a silanol group presented on a surface of the inorganic filler included in the resin cured material. However, there is a problem that an adhesive stability is low in case that an area of an inorganic filler exposed to a surface of the resin cured material is small because a surface of an inorganic filler is covered with a polymerizable monomer. Further, a high degree of polymerization of a resin cured material is a factor for decreasing of an adhesive stability, because an unreacted polymerizable group scarcely remains on a surface of the resin cured material, and a co-polymerizable is hardly generated between the resin cured material and an adhesive agent.

Japanese Unexamined Patent Application Publication No. H08-277207 (JPH8-277207 A) and Japanese Unexamined Patent Application Publication No. H10-109916 (JPH10-109916 A) disclose an adhesive agent for a dental resin composite material used in built-up of an unpolymerized acrylic resin-based composite material on a cured composite resin. More specifically, JPH8-277207 A and JPH10-109916 A disclose that because monomers enter into fine concave and convex present on a surface of a cured composite resin by compounding tetrahydrofurfuryl methacrylate having a high wettability to a resin material, an adhesive strength increases by increasing a mechanical fitting force. However, the adhesive strength does not reach a sufficient level in an actual clinical application.

Japanese Unexamined Patent Application Publication No. 2006-45094 (JP2006-45094 A) discloses a primer composition which can impart a high adhesive strength while bonding a dental prosthesis article consisting of a resin cured material, and a dentin and/or other dental material. More specifically, JP2006-45094 A discloses that the primer composition includes a polymerizable monomer having an acidic group such as 11-(meth)acryloyloxyundecane-1,1-dicarboxylic acid, an aromatic amine such as ethyl p-dimethylaminobenzoate, and a volatile organic solvent such as acetone, and these three components are divided into two liquids and preserved. In JP2006-45094 A, this primer composition exhibits an excellent adhesive property to the resin cured material without change of the nature such as gelling when the two liquids are mixed just before the use. However, when the polymerizable monomer having an acidic group and the aromatic amine coexist in the primer composition, change of the nature such as gelling may occur by acid-base reaction of two components. Therefore, there is a problem that because it is necessary to divide these components into two liquids and mix the two liquids just before the use, operation is complicated.

Japanese Unexamined Patent Application Publication No. 2015-20977 (JP2015-20977 A) discloses a dental adhesive composition having adhesive property to a prosthesis article consisting of a resin cured material, a ceramic, a noble metal and a no-noble metal etc. This dental adhesive composition includes a silane coupling agent having a polymerizable group, a tiopropionic acid derivative or a thioglycolic acid derivative, and a volatile solvent and has a feature that the dental adhesive composition may be used for wide applications because the tiopropionic acid derivative or the thioglycolic acid derivative exhibits an adhesive property to a dental noble metal, and the silane coupling agent exhibits an adhesive property to a resin cured material and a ceramic. However, because the tiopropionic acid derivative and the thioglycolic acid derivative exhibit acidity, there is a problem that when the tiopropionic acid derivative or the thioglycolic acid derivative is made into one liquid with the silane coupling agent, a sufficient adhesive property to a resin cured material cannot obtained since hydrolysis and condensation of the silane coupling agent gradually advance.

An object of the present invention is to provide a dental primer composition for a prosthesis article having a high adhesive stability to a resin cured material having a high degree of polymerization by thermal polymerizing and/or photo polymerizing.

SUMMARY OF THE INVENTION

In order to solve the above problem, the present inventors found a following knowledge as a result of intensive studies.

That is, it has been found by the present inventors that there is a strong correction between an adhesive property to a resin cured material and a solubility parameter (hereinafter referred to as "SP value") of a polymerizable monomer included in a primer, and that the problem is solved by compounding a polymerizable monomer having a solubility parameter (an SP value) in the range of from 7.0 to 10.0.

More specifically, a resin cured material includes a cured material of (meth) acrylate-base material such as urethane dimethacrylate (UDMA), 2,2-bis(4-(3-(meth)acryloyloxy-2- hydroxypropoxy)phenyl)propane (Bis-GMA) and triethylene glycol dimethacrylate (TEGDMA), and an inorganic filler as a main component. Because a wettability between a resin cured material and a primer composition depends on polarities thereof, that is, hydrophilicity/hydrophobicity, an improvement of an adhesive property can be expected by approximating a polarity of a primer composition to that of a resin cured material. Therefore, the present inventors focus attention on a solubility parameter (an SP value) which is an index of hydrophilicity/hydrophobicity, and as a result of intensive studies, the knowledge that an excellent adhesive property is exhibited by compounded with a polymerizable monomer having a solubility parameter (an SP value) in the range of from 7.0 to 10.0 in a primer composition, was obtained. Although a detail of an adhesive mechanism of the present disclosure is unknown, it is thought that an adhesive property increase by permeation of a part of (A) a polymerizable monomer having a solubility parameter (an SP value) in the range of from 7.0 to 10.0 to a surface layer of a resin cured article or by impregnation of a part of (A) a polymerizable monomer having a solubility parameter in the range of from 7.0 to 10.0 to an interface of a polymerizable monomer polymerized with an inorganic filler in a resin cured material.

Specifically, the present disclosure provides a primer composition for a resin cured material, comprising (A) a polymerizable monomer having a solubility parameter (an SP value) in the range of from 7.0 to 10.0, (B) a volatile organic solvent, (C) a polymerization catalyst and/or a polymerization accelerator, and (D) a polymerizable monomer having at least two polymerizable group.

In the present disclosure, a molecular weight of the polymerizable monomer having a solubility parameter (an SP value) in the range of from 7.0 to 10.0 (A) is preferably 150 or less, and a content of the polymerizable monomer having a solubility parameter (an SP value) in the range of from 7.0 to 10.0 (A) is preferably 5.0 to 60.0 parts by weight based on 100 parts by weight of a total content of the polymerizable monomer having a solubility parameter (an SP value) in the range of from 7.0 to 10.0 (A), the volatile organic solvent (B), and the polymerizable monomer having at least two polymerizable group (D). Further, an aromatic amine is preferably compounded as the polymerization catalyst and/or a polymerization accelerator (C) in the present disclosure.

The present disclosure provides a dental primer composition for a prosthesis article having a high adhesive stability to a resin cured material having a high degree of polymerization by thermal polymerizing and/or photo polymerizing.

DETAILED DESCRIPTION OF THE PREFERRED EMBODIMENTS

A primer composition for a resin cured material of the present disclosure will be described below.

A primer composition for a resin cured material of the present disclosure comprises (A) a polymerizable monomer having a solubility parameter (an SP value) in the range of from 7.0 to 10.0, (B) a volatile organic solvent, (C) a polymerization catalyst and/or a polymerization accelerator, and (D) a polymerizable monomer having at least two polymerizable group.

In the present disclosure, the solubility parameter (an SP value) of (A) a polymerizable monomer having a solubility parameter (an SP value) in the range of from 7.0 to 10.0 can be determined by calculation according to the formulation of Fedors calculation method which is described in "Polymer Eng. & Sci., vol. 14, No. 2 (1974), pages 148 to 154)", represented by following formula (1).

$$\text{SP value} = (\Sigma \Delta ei / \Sigma \Delta vi)^{1/2} \quad \text{[formula (1)]}$$

(in which "$\Delta ei$" is evaporation energy at 25° C. attributing to atoms or groups, and "$\Delta vi$" is the molar volume at 25° C.)

$\Delta ei$ and $\Delta vi$ in the above numerical formula indicate definite numerical values given to i atoms and groups in a main molecule. Further, typical examples of the numerical values of $\Delta ei$ and $\Delta vi$ given to the atoms or groups are shown in the following Table 1:

TABLE 1

| Atom or group | $\Delta e$ (cal/mol) | $\Delta V$ (cm³/mol) |
|---|---|---|
| —CH₃ | 1125 | 33.5 |
| —CH₂— | 1180 | 16.1 |
| —CH< | 820 | −1 |
| >C< | 350 | −19.2 |
| =CH₂ | 1030 | 28.5 |
| —CH= | 1030 | 13.5 |
| >CH= | 920 | −5.5 |
| HC≡ | 1690 | 27.4 |
| —CE≡ | 7630 | 6.5 |
| Ph— | 7630 | 71.4 |
| —Ph— | 7630 | 52.4 |
| >Ph— | 7630 | 33.4 |
| >Ph< | 7630 | 14.4 |
| ∍Ph< | 7630 | −4.6 |
| ∍Ph∈ | 7630 | −23.6 |
| Five or more membered ring | 250 | 16 |
| Three or four membered ring | 750 | 18 |
| Ring have conjugated doble bond | 400 | −2.2 |
| —COOH | 6600 | 28.5 |
| —COO— | 4300 | 18 |
| >C=O | 4150 | 10.8 |
| —CHO | 5100 | 22.3 |
| —CO-O—CO— | 7300 | 30 |
| —CONH₂ | 10000 | 17.5 |
| —CONH— | 8000 | 9.5 |
| —CON< | 7050 | −7.7 |
| HCON< | 6600 | 11.3 |
| HCONH— | 10500 | 27 |
| —COCl | 5000 | 38 |
| NH₂ | 3000 | 19 |
| —NH— | 2000 | 4.5 |
| —N< | 1000 | −9 |
| —N= | 2800 | 5 |
| —CN | 6100 | 24 |
| —NO(aliphatic) | 7000 | 24 |
| —NO₂(aromatic) | 3670 | 32 |
| —NCO | 6800 | 35 |
| —O— | 800 | 3.8 |
| —OH | 7120 | 10 |
| —OH(adjacent C or disubstituted) | 6220 | 13 |
| Si | 810 | 0 |

SP value of butyl acrylate which is shown by the follow structural formula, calculated by the above formula is as follow:

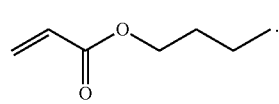

[Formula 1]

Butyl acrylate includes one =CH₂ group, one —CH=group, one —COO— group, three —CH₂— groups, one —CH₃ group. Therefore, $\Sigma \Delta ei$ of butyl acrylate is 1030+1030+4300+1180×3+1125=11025 (cal/mol). And Σvi of butyl acrylate is 28.5+13.5+18+16.1×3+33.5=141.8 (cm³/mol). Accordingly, SP value of butyl acrylate is $(\Sigma \Delta ei/\Sigma \Delta vi)^{1/2}$=8.8 (cal/cm³).

Specific examples of the polymerizable monomer having a solubility parameter (an SP value) in the range of from 7.0 to 10.0 (A) in the present disclosure include a polymerizable monomer having one polymerizable group, such as methyl acrylate, methyl methacrylate, ethyl acrylate, butyl acrylate, butyl methacrylate, pentyl acrylate, pentyl methacrylate, hexyl methacrylate and nonyl methacrylate. Among these polymerizable monomer, from the view point of a permeability or a impregnant ability, the polymerizable monomers having a solubility parameter (an SP value) (A) in the range of from 7.0 to 10.0 having a molecular weight of 150 or less (150 g/mol or less of molar mass) are preferable, and in the present disclosure, methyl acrylate and methyl methacrylate are preferable. If a polymerizable monomer having a solubility parameter (an SP value) of more than 10.0 or of less than 7.0 is used, because a wettability to a resin cured material is decrease, an adhesive property decrease.

In the present disclosure, the polymerizable monomer having a solubility parameter (an SP value) in the range of from 7.0 to 10.0 (A) can be used singly or in combinations of several types. A content of the polymerizable monomer having a solubility parameter (an SP value) in the range of from 7.0 to 10.0 (A) is preferably 5.0 to 60.0 parts by weight, more preferably 10.0 to 40.0 parts by weight, and further more preferably 15.0 to 30.0 parts by weight, based on 100 parts by weight of a total content of the polymerizable monomer having a solubility parameter (an SP value) in the range of from 7.0 to 10.0 (A), the volatile organic solvent (B), and the polymerizable monomer having at least two polymerizable group (D). If the content of the polymerizable monomer having a solubility parameter (an SP value) in the range of from 7.0 to 10.0 (A) is less than 5.0 parts by weight, an adhesive stability may decrease because a permeability or a impregnant ability to a resin cured material may decrease, and if the content of the polymerizable monomer having a solubility parameter (an SP value) in the range of from 7.0 to 10.0 (A) is more than 60.0 parts by weight, an adhesive stability may be impaired because a polymerizability of a primer composition may significantly decrease.

In the present disclosure, the volatile organic solvent (B) means an organic solvent having a boiling point of 100° C. or less under 760 mmHg, and a vapor pressure of 1.0 Kpa or more at 20° C., and includes methanol, ethanol, n-propanol, isopropyl alcohol, acetone, methyl ethyl ketone as specific examples. In the present disclosure, ethanol, isopropyl alcohol and acetone are preferable in consideration of harmful to the living body.

In the present disclosure, the volatile organic solvent (B) can be used singly or in combinations of several types. A content of the volatile organic solvent (B) is preferably 5.0 to 50.0 parts by weight, more preferably 10.0 to 40.0 parts by weight, and further more preferably 10.0 to 30.0 parts by weight, based on 100 parts by weight of a total content of the polymerizable monomer having a solubility parameter (an SP value) in the range of from 7.0 to 10.0 (A), the volatile organic solvent (B), and the polymerizable monomer having at least two polymerizable group (D). If the content of the volatile organic solvent (B) is less than 5.0 parts by weight, an operability may decrease because a viscosity of a primer composition may increase. On the other hand, if the content of the volatile organic solvent (B) is more than 50.0 parts by weight, an adhesive stability may decrease because a polymerizability of a primer composition may significantly decrease by remaining an organic solvent in an adhesive layer due to lowering of a volatility.

In the present disclosure, for the polymerization catalyst (C), any polymerization catalysts may be used as long as it may initiate polymerization of a polymerizable monomer by heat, light, or redox reaction, and may be optionally selected from the group consisting of an organic peroxide, an inorganic peroxide, α-diketone, and an acylphosphine oxide.

Examples of the organic peroxide include diacyl peroxides, peroxyesters, dialkyl peroxides, peroxyketals, ketone peroxides, and hydroperoxides. Specific examples of the diacyl peroxides include benzoyl peroxide, 2,4-dichlorobenzoyl peroxide, m-toluoylbenzoyl peroxide. Specific examples of peroxyesters include t-butyl peroxybenzoate, bis (t-butylperoxy)isophthalate, 2,5-dimethyl-2,5-bis(benzoylperoxy)hexane, t-butyl peroxy-2-ethylhexanoate, and t-butyl peroxy isopropyl carbonate. Specific examples of dialkyl peroxides include dicumyl peroxide, di-t-butyl peroxide, and lauroyl peroxide. Specific examples of peroxyketals include 1,1-bis(t-butylperoxy)-3,3,5-trimethylcyclohexane. Specific examples of ketone peroxides include methyl ethyl ketone peroxide. Specific examples of hydroperoxides include p-menthane hydroperoxide, diisopropylbenzene hydroperoxide, 1,1,3,3-tetramethylbutyl hydroperoxide, cumene hydroperoxide, t-hexyl hydroperoxide, t-butyl hydroperoxide, t-amyl hydroperoxide, and pinane hydroperoxide. In the present disclosure, benzoyl peroxide and cumene hydroperoxide are preferable.

Examples of the inorganic peroxide include peroxodisulfate and peroxodiphosphate. Specific examples of the peroxodisulfate include sodium peroxodisulfate, potassium peroxodisulfate, aluminum peroxodisulfate, and ammonium peroxodisulfate. Specific examples of the peroxodiphosphate include sodium peroxodiphosphate and potassium peroxodiphosphate.

As to α-diketone, a known compound having α-diketone structure can be used without any limitation. Specific examples of α-diketone include camphorquinones such as camphorquinone, camphorquinonecarboxylic acid and camphorquinonesulfonic acid, diacetyl, acetylbenzoyl, benzyl, 4,4'-dimethoxybenzil, 4,4'-oxybenzyl, 2,3-pentadione, 2,3-octadione, 9,10-phenanthrenequinone, acenaphthenequinone, 1,2-cyclohexanedione, and o-benzoquinone. In the present disclosure, from the view point of polymerizability, camphorquinones are preferable.

Examples of the acylphosphine oxides include 2,4,6-trimethylbenzoyldiphenylphosphine oxide, 2,6-dimethylbenzoylphenylphosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, methyl 2,4,6-trimethylbenzoylphenylphosphinate, ethyl 2,4,6-trimethylbenzoylphenylphosphinate, phenyl 2,4,6-trimethylbenzoylphenylphosphinate. In the present disclosure, from the view point of polymerizability, 2,4,6-trimethylbenzoyldiphenylphosphine oxide and alkyl 2,4,6-trimethylbenzoylphenylphosphinate are preferable.

Examples of the polymerization accelerator (C) of the present disclosure include aromatic amines, aliphatic amines, aromatic sulfonates and sulfites, and barbituric acids and derivative thereof. In the present disclosure, aromatic amines are preferably compounded as the polymerization accelerator (C). Because aromatic amines exhibit a strong reducing property, aromatic amines may be used as a reducing agent for a wide variety of a polymerization catalyst. Therefore, a stable adhesive property can be obtained by highly porimerization near the bonding interface.

For the aromatic amine, a known aromatic secondary amine and aromatic tertiary amine can be used. Specific examples of the aromatic secondary amine and the aromatic tertiary amine include N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, and ethyl 4-N,N-dimethylaminobenzoate. In the present disclosure, from the view point of polymerizability, the aromatic tertiary amine is preferable, and N,N-di(2-hydroxyethyl)-p-toluidine and N,N-dimethyl-m-toluidine are more preferable.

Specific examples of the aliphatic amine include primary aliphatic amines such as n-butylamine, n-hexylamine, and n-octylamine; secondary aliphatic amines such as diisopropylamine, dibutylamine, and N-methylethanolamine; and tertiary aliphatic amines such as N-methyldiethanolamine, N-ethyldiethanolamine, N-n-butyldiethanolamine, N-lauryldiethanolamine, 2-(dimethylamino)ethyl (meth) acrylate, N-methyldiethanolamine di(meth)acrylate, N-ethyldiethanolamine di(meth)acrylate, triethanolamine tri(meth)acrylate, triethanolamine, trimethylamine, triethylamine, and tributylamine. In the present disclosure, from the view point of polymerizability, tertiary aliphatic amines are preferable, 2-(dimethylamino) ethyl (meth)acrylate is more preferable.

Specific examples of the aromatic sulfonate include lithium salts, sodium salts, potassium salts, rubidium salts, cesium salts, magnesium salts, calcium salts, strontium salts, iron salts, cupper salts, zinc salts, ammonium salts, tetramethyl ammonium salts and tetraethyl ammonium salts of benzene sulfinic acid, p-toluene sulfinic acid, o-toluene sulfinic acid, ethyl benzene sulfinic acid, decyl benzene sulfinic acid, dodecyl benzene sulfinic acid, 2,4,6-trimethyl benzene sulfinic acid, 2,4,6-triisopropyl benzene sulfinic acid, chlorobenzene sulfinic acid, and naphthalene sulfinic acid. In the present disclosure, from the view point of polymerizability, p-toluene sulfinic acid and sodium salts thereof are preferable.

Specific examples of the sulfite include sodium sulfite, potassium sulfite, calcium sulfite, and ammonium sulfite. Specific examples of the bisulfite include sodium bisulfite and potassium bisulfite.

Specific examples of the barbituric acids and derivatives thereof include barbituric acids, tiobarbituric acids, 1,3,5-trimethylbarbituric acid, 1-phenyl-5-benzylbarbituric acid, 1-benzyl-5-phenylbarbituric acid, 1,3-dimethylbarbituric acid, 1,3-dimethyl-5-phenylbarbituric acid, 1-cyclohexyl-5-ethylbarbituric acid, 5-laurylbarbituric acid, 5-butylbarbituric acid, 5-allylbarbituric acid, 5-phenyltiobarbituric acid, 1,3-dimethyltiobarbituric acid, trichlorobarbituric acid, 5-nitrobarbituric acid, 5-aminobarbituric acid and 5-hidroxybarbituric acid, and sodium salts, calcium salts and potassium salts thereof. In the present disclosure, from the view point of polymerizability, 1,3,5-trimethylbarbituric acid and 1-phenyl-5-benzylbarbituric acid, and sodium salts and calcium salts thereof are preferable.

In the present disclosure, the polymerization catalyst and/or a polymerization accelerator (C) can be used singly or in combinations of several types. A content of the polymerization catalyst and/or a polymerization accelerator (C) is preferably 0.1 to 20.0 parts by weight, more preferably 0.2 to 15.0 parts by weight, and further more preferably 4.0 to 8.0 parts by weight, based on 100 parts by weight of a total content of the polymerizable monomer having a solubility parameter (an SP value) in the range of from 7.0 to 10.0 (A), the volatile organic solvent (B), and the polymerizable monomer having at least two polymerizable group (D). If the content of the polymerization catalyst and/or a polymerization accelerator (C) is less than 0.1 parts by weight, an adhesive strength may decrease because a polymerization activity may be insufficient. On the other hand, if the content of the polymerization catalyst and/or a polymerization accelerator (C) is more than 20 parts by weight, it may be difficult to secure a sufficient operational surplus time.

In the present disclosure, the polymerizable monomer having at least two polymerizable group (D) is used for increasing a polymerizability of a primer composition. A content of the polymerizable monomer having at least two polymerizable group (D) is preferably 20.0 to 80.0 parts by weight, more preferably 30.0 to 75.0 parts by weight, and further more preferably 40.0 to 70.0 parts by weight, based on 100 parts by weight of a total content of the polymerizable monomer having a solubility parameter (an SP value) in the range of from 7.0 to 10.0 (A), the volatile organic solvent (B), and the polymerizable monomer having at least two polymerizable group (D). It should be noted that although the type of polymerizable monomer of the polymerizable monomer having at least two polymerizable group (D) is preferably different from that of the polymerizable monomer having a solubility parameter (an SP value) in the range of from 7.0 to 10.0 (A), the type of polymerizable monomer of the polymerizable monomer having at least two polymerizable group (D) may be the same as that of the polymerizable monomer having a solubility parameter (an SP value) in the range of from 7.0 to 10.0 (A). If the content of the polymerizable monomer having at least two polymerizable group (D) is less than 20 parts by weight, a polymerizability of a primer composition may decrease to impair an adhesive stability, and if the content of the polymerizable monomer having at least two polymerizable group (D) is more than 70 parts by weight, a viscosity of a primer composition may increase to significantly impair operability. Examples of such polymerizable monomer having at least two polymerizable group (D) include an aromatic compound-based bifunctional polymerizable monomer, an aliphatic compound-based bifunctional polymerizable monomer, and a trifunctional or higher polymerizable monomer.

Specific examples of the aromatic compound-based bifunctional polymerizable monomer include 2,2-bis((meth)acryloyloxyphenyl)propane, 2,2-bis[4-(3-(meth)acryloyloxy)-2-hydroxypropoxyphenyl]propane (Bis-GMA), 2,2-bis(4-(meth)acryloyloxyethoxyphenyl)propane, 2,2-bis(4-(meth)acryloyloxypolyethoxyphenyl)propane, 2,2-bis(4-(meth)acryloyloxydiethoxyphenyl)propane, 2,2-bis(4-(meth)acryloyloxytriethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2-(4-(meth)acryloyloxydiethoxyphenyl)-2-(4-(meth)acryloyloxyethoxyphenyl)-propane, 2-(4-(meth)acryloyloxydiethoxyphenyl)-2-(4-(meth)acryloyloxytriethoxy-phenyl)propane, 2-(4-(meth)acryloyloxydipropoxyphenyl)-2-(4-(meth)acryloyloxytriethoxy-phenyl)propane, 2,2-bis(4-(meth)acryloyloxypropoxyphenyl)propane, 2,2-bis(4-(meth)acryloyloxyisopropoxyphenyl)propane, and 1,4-bis(2-

(meth)acryloyloxyethyl)pyromeritate. Among these, 2,2-bis[4-(3-(meth)acryloyloxy)-2-hydroxypropoxyphenyl]propane is preferable.

Specific examples of the aliphatic compound-based bifunctional polymerizable monomer include erythritol di(meth)acrylate, sorbitol di(meth)acrylate, mannitol di(meth)acrylate, pentaerythritol di(meth)acrylate, dipentaerythritol di(meth)acrylate, glycerol di(meth)acrylate, ethylene glycol di(meth)acrylate, diethylene glycol di(meth)acrylate, triethylene glycol di(meth)acrylate (TEGDMA), propylene glycol di(meth)acrylate, butylene glycol di(meth)acrylate, neopentyl glycol di(meth)acrylate, polyethylene glycol di(meth)acrylate, 1,3-butanediol di(meth)acrylate, 1,5-pentanediol di(meth)acrylate, 1,6-hexanediol di(meth)acrylate, 1,10-decanediol di(meth)acrylate, 2,2,4-trimethylhexamethylenebis(2-carbamoyloxyethyl)dimethacrylate (UDMA), and 1,2-bis(3-methacryloyloxy-2-hydroxypropoxy)ethane. Among these, glycerol di(meth)acrylate, triethylene glycol di(meth)acrylate, 2,2,4-trimethylhexamethylenebis(2-carbamoyloxyethyl)dimethacrylate, and 1,2-bis(3-methacryloyloxy-2-hydroxypropoxy)ethane are preferable.

Specific examples of the trifunctional or higher polymerizable monomer include trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, dipentaerythritol tri (meth)acrylate, dipentaerythritol tetra(meth)acrylate, dipentaerythritol penta(meth)acrylate, N,N-(2,2,4-trimethylhexamethylene)bis[2-(aminocarboxy)propane-1,3-diol] tetramethacrylate, and 1,7-diacryloyloxy-2,2,6,6-tetraacryloyloxymethyl-4-oxyheptane.

The primer composition of the present disclosure may be compounded with a polymerizable monomer having an acidic group in order to impart an adhesive property to a dentine or a metal material. Examples of the acid group include a radical acid group such as a phosphinico group [=P(=O)OH], a phosphono group [—P(=O)(OH)$_2$], a carboxyl group (—C(=O)OH), and sulfo group (—SO$_3$H), and an acid anhydride obtained by dehydration condensation of these two acid group (for example, —C(=O)—O—C(=O)—).

The primer composition of the present disclosure may be compounded with a silane coupling agent in order to impart an adhesive property to a dental ceramic material. As the silane coupling agent, known silane coupling agent may be used without any limitation. A coupling agent is a surface treatment agent which may bond an organic material and an inorganic material, and is a compound which has a polymerizable group and a hydolyzable group in a molecule. In the present disclosure, γ-methacryloxypropyl trimethoxy silane and γ-methacryloxypropyl tri (trimethl siloxy) silane are preferably used.

As to the primer composition of the present disclosure, other component such as an excipient typified by fumed silica, an ultraviolet absorber such as 2-hydroxy-4-methylbenzophenone, a polymerization inhibitor such as hydroquinone, hydroquinone monomethyl ether and 2,5-di-t-butyl-4-methylphenol, a discoloration inhibitor, an antibacterial material, a coloring pigment, or other conventionally known additive can be added arbitrarily, if necessary, in addition to the above components (A) to (D).

EXAMPLES

Hereinafter, the present disclosure will be described with reference to Examples. However, the present disclosure is not limited to Examples. Abbreviations and test methods used in examples are as follows. Further, structural formulas, SP values, and/or molecular weights are shown in Table. 2 and Table. 7.

[(A) A Polymerizable Monomer Having a Solubility Parameter (an Sp Value) in the Range of From 7.0 to 10.0]
MAA: methyl acrylate (molecular weight: 86.0)
MMA: methyl methacrylate (molecular weight: 100.1)
BAA: butyl acrylate (molecular weight: 128.2)
HMA: hexyl acrylate (molecular weight: 170.3)
NMA: nonyl methacrylate (molecular weight: 212.3)

TABLE 2

| Polymerizable monomer | Structure | SP value |
|---|---|---|
| MAA Methyl acrylate | 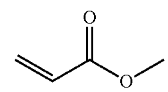 | 9.0 |
| MMA Methyl methacrylate | 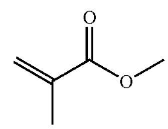 | 8.2 |
| BAA Butyl acrylate | 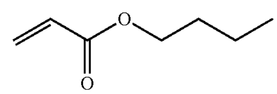 | 8.8 |
| HMA Hexyl acrylate | 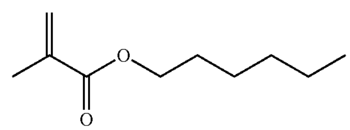 | 8.4 |
| NMA Nonyl methacrylate | 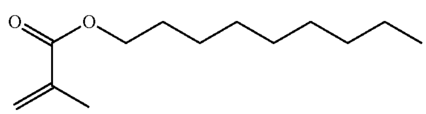 | 9.1 |

[(B) A Volatile Organic Solvent]
EtOH: anhydrous ethanol
[(C) A Polymerization Catalyst and/or a Polymerization Accelerator]
DMPT: N,N-diethyl-m-toluidine
DEPT: N,N-di(2-hydroxyethyl)-p-toluidine
BPBA: 1-phenyl-5-benzylbarbituric acid
CQ: camphor quinone
APO: 2,4,6-trimethylbenzoyldiphenylphosphine oxide
DMBE: ethyl N,N-dimethylaminobenzoate
pTNa: sodium p-Toluenesulfinate
BPO: benzoyl peroxide
[(D) A Polymerizable Monomer Having at Least Two Polymerizable Group]
Bis-GMA: 2,2-bis[4-(3-(meth)acryloyloxy)-2-hydroxypropoxyphenyl]propane
TEGDMA: triethylene glycol di(meth)acrylate
[Other Component]
2-HEMA: 2-hydroxyethyl methacrylate
R-7200: Particulate silica, Aerosil R-7200 (manufactured by Nippon Aerosil Co., Ltd.)
BHT: 2,5-di-t-butyl-4-methylphenol
[Measurement Method of Initial Adhesive Property and Adhesive Durability]

A block piece (12 mm×14 mm×3.0 mm) was prepared by cut out from the dental resin cured material for CAD/CAM "SHOFU Block HC" (manufactured by SHOFU Inc.) using "Sectom" (manufactured by Marumoto Struers K.K.). One surface of the block piece was polished with SiC #600, then was washed with water and dried with air. Further, the one surface was sandblasted with alumina having an average particle size of about 50 μm (with 0.2-0.3 MPa) then was washed with water and dried with air to prepare a test specimen. The one surface of test specimen was adhered with a tape having a round hole having a thickness of 200 μm and a diameter of 3.5 mm. A part of the one surface exposed in the round hole, was applied with a primer composition (in case of two-packs type primer composition, this primer composition is a liquid prepared by equally mixing two liquids) and dried with air.

On the other hand, a stainless rod (having a diameter of 4.55 mm) having an adhesive surface which is sandblasted with alumina having an average particle size of about 50 μm (with 0.3-0.5 MPa) then is washed with water and dried with air, thereafter, is applied with a metal primer "Metal Link" (manufactured by SHOFU Inc.) and is dried with air for 10 seconds, was used as a tool for adhesive test. The adhesive surface of the stainless rod was applied with a kneaded material of a dental adhesive resin cement "ResiCem" (manufactured by SHOFU Inc.), and the kneaded material was pressure contacted with the stainless rod so as to overwrapping the round hole having the diameter of 3.5 mm with the center of the stainless rod. Thereafter, the kneaded material was applied with load of 200 g and was place statically for 30 seconds. After removing excess paste by a micro brush, the load was removed, and light was irradiated from the block test specimen side to the stainless rod for 10 seconds using "Blue Shot" (manufactured by SHOFU Inc.). After immersion in 37° C. for 24 hours, an initial tensile adhesive strength for the test specimen (the number of the test specimen is 6) was measured at 1 ram/min of crosshead speed by Instron Universal Testing Machine (Instron 5567; manufactured by Instron Corporation). Further, after immersion in 37° C. for 24 hours and then 5000 times of thermal cycle (4° C.<-->60° C., immersion in each temperature for 1 minute) was applied, a tensile adhesive durability strength for the test specimen (the number of the test specimen is 6) was measured.

When both an initial adhesive property and an adhesive durability of the test specimen were 1.0 MPa or more, the test specimen was determined to have a usable adhesive strength. When both an initial adhesive property and an adhesive durability of the test specimen were 10.0 MPa or more, the test specimen was determined to have a strong adhesive strength.

Operability (1) Application Property

A block piece (12 mm×14 mm×3.0 mm) was prepared by cut out from the dental resin cured material for CAD/CAM "SHOFU Block HC" (manufactured by SHOFU Inc.) using "Sectom" (manufactured by Marumoto Struers K.K.). Evaluation was made with respect to an application property in applying a primer composition (in case of two-packs type primer composition, the primer composition is a liquid prepared by equally mixing two liquids) to this block piece using a micro brush.

The rating criteria are as follows.

A: Having moderate viscosity and can be applied uniformly.
B: Having viscosity can be applied, but cannot be applied uniformly.
C: Having extremely high (or low) viscosity and cannot be applied uniformly.

(2) Air Dry Ability

Evaluation was made with respect to a dry ability after air drying for 5 seconds to the above described block piece applied with a primer composition.

The rating criteria are as follows.

A: Solvent is removed with air of the low pressure quickly and a uniform film is formed.
B: Solvent is removed by increasing air pressure and a uniform film is formed.
C: Uniform film is not formed by air drying.

[Method of Preparing One-Pack Type Primer Composition]

One-pack type primer compositions (Compositions 1-42) were prepared by loading materials shown in Table 3 into a container under light shielding, and then stirring and mixing the materials by Turbula mixer (T2F: manufactured by Shinmaru Enterprises Corp.) for 24 hours, and confirming that the resultant is in a dissolved state.

TABLE 3

| | (A) a polymerizable monomer having a solubility parameter (an SP value) in the range of from 7.0 to 10.0 | | | | | (B) a volatile organic solvent | | (C) a polymerization catalyst and/or a polymerization accelerator | | | | | | |
|---|---|---|---|---|---|---|---|---|---|---|---|---|---|---|
| | MAA | MMA | BAA | HMA | NMA | Aceton | EtOH | DMPT | DEPT | BPBA | CQ | APO | DMBE | pTNa |
| SP value | 9 | 8.2 | 8.8 | 8.4 | 8.4 | — | — | — | — | — | — | — | — | — |
| Molecular weight (g/mol) | 86 | 100.1 | 128.2 | 170.3 | 212.3 | — | — | — | — | — | — | — | — | — |
| Composition 1 | 20 | | | | | 20 | | 3 | | | 1 | | 1 | |
| Composition 2 | | 25 | | | | 10 | | 4 | | | 2 | | 1 | |
| Composition 3 | | | 15 | | | | 25 | 2 | | | 1 | | 1 | |
| Composition 4 | 20 | | | | | 30 | | 2 | | | 1 | | 1 | |
| Composition 5 | | 30 | | | | 15 | | 2 | | | | 1 | | 1 |
| Composition 6 | | 30 | | | | | 15 | 4 | | | | | | |
| Composition 7 | | 20 | | | | 10 | | | 6 | | | | | 1 |
| Composition 8 | 15 | | | | | | 30 | | 6 | | 1 | | 1 | |
| Composition 9 | 30 | | | | | 10 | | 4 | | | 1 | | 1 | |
| Composition 10 | | | 30 | | | 15 | 10 | 4 | | | 1 | | | |
| Composition 11 | 15 | 15 | | | | 15 | | | 4 | | 1 | | | 1 |
| Composition 12 | | 20 | | | | 10 | 10 | 2 | 2 | | | | | |
| Composition 13 | | 15 | | | | 25 | 5 | 2 | 2 | | 1 | | 1 | |
| Composition 14 | | | 20 | | | 5 | 5 | 2 | 2 | | 1 | | 1 | |
| Composition 15 | 25 | | | | | 20 | | 2 | 2 | | 1 | | 1 | |
| Composition 16 | | 10 | 5 | | | 15 | | 2 | 2 | | 1 | | 1 | |
| Composition 17 | 20 | | 10 | | | 20 | | 6 | | | | | | |
| Composition 18 | | 30 | | | | 10 | 20 | 4 | | | 1 | | 1 | |

TABLE 3-continued

| | | | | | | | | | | |
|---|---|---|---|---|---|---|---|---|---|---|
| Composition 19 | | | 20 | | 20 | 4 | | | 1 | 1 |
| Composition 20 | 5 | 5 | 10 | | 25 | 4 | | | 1 | 1 |
| Composition 21 | | 5 | | | 40 | 3 | | | 1 | 1 |
| Composition 22 | | 20 | 20 | | 10 | | 5 | | 1 | 1 |
| Composition 23 | | | 50 | | 5 | | 5 | | 1 | 1 |
| Composition 24 | | | 15 | | 20 | 20 | 3 | | 1 | 1 |
| Composition 25 | | 15 | | | 40 | | 5 | | 1 | 1 |
| Composition 26 | | 10 | | | 10 | | 5 | | 1 | 1 |
| Composition 27 | | | | 20 | 20 | | 3 | | 1 | 1 |
| Composition 28 | | 20 | | | | 50 | 3 | | 1 | 1 |
| Composition 29 | 30 | 30 | | | 10 | | 3 | | 1 | 1 |
| Composition 30 | | | 35 | | 25 | | 3 | | 1 | 1 |
| Composition 31 | | | | | 30 | | 3 | | 1 | 1 |
| Composition 32 | | | | 15 | | 30 | 3 | | 1 | 1 |
| Composition 33 | | | | | | | 3 | | 1 | 1 |
| Composition 34 | 1 | | | | 30 | | 5 | | 1 | 1 |
| Composition 35 | | 1 | | | 30 | | 5 | | 1 | 1 |
| Composition 36 | | 10 | | | 5 | | 3 | | 1 | 1 |
| Composition 37 | | | | 30 | | | 3 | | 1 | 1 |
| Composition 38 | | 70 | | | 5 | | 5 | | 1 | 1 |
| Composition 39 | | 15 | | | 60 | | 5 | | 1 | 1 |
| Composition 40 | | 50 | | | 35 | | 3 | | 1 | 1 |
| Composition 41 | 15 | 15 | | | 15 | | 0.05 | | 1 | 1 |
| Composition 42 | 15 | 15 | | | 15 | | 10 | 10 | 1 | 1 |
| Composition 43 | | 20 | | | 10 | | | | 1 | 4 |
| Composition 44 | | 20 | | | 10 | 1 | | | | |
| Composition 45 | | 20 | | | 10 | 10 | | | | |

| | | (D) a polymerizable monomer having at least two polymorizable group | | | Other component additives etc. | | |
|---|---|---|---|---|---|---|---|
| | | UDMA | Bis-GMA | TEGDMA | 2-HEMA | R-7200 | BHT | Total |
| | SP value | 10.5 | 11 | 9 | 10.4 | — | — | — |
| | Molecular weight (g/mol) | 470.6 | 512.6 | 286.3 | 130.1 | — | — | — |
| | Composition 1 | 45 | | 15 | | 3 | 0.1 | 108.1 |
| | Composition 2 | | 40 | 25 | | | 0.1 | 107.1 |
| | Composition 3 | 40 | | 20 | | | 0.1 | 104.1 |
| | Composition 4 | 40 | | 10 | | | 0.1 | 104.1 |
| | Composition 5 | 55 | | | | | 0.1 | 104.1 |
| | Composition 6 | 25 | | 30 | | 5 | 0.1 | 112.1 |
| | Composition 7 | 30 | | 40 | | | 0.1 | 108.1 |
| | Composition 8 | | 20 | 35 | | | 0.1 | 108.1 |
| | Composition 9 | 60 | | | | | | 106 |
| | Composition 10 | | 20 | 25 | | | | 105 |
| | Composition 11 | 10 | 25 | 20 | | | | 106 |
| | Composition 12 | 40 | | 20 | | 5 | 0.2 | 110.2 |
| | Composition 13 | 25 | 10 | 20 | | | 0.1 | 106.1 |
| | Composition 14 | 15 | 15 | 40 | | | 0.1 | 106.1 |
| | Composition 15 | 55 | | | | 2 | 0.1 | 108.1 |
| | Composition 16 | 40 | | 30 | | | 0.1 | 106.1 |
| | Composition 17 | 25 | 15 | 10 | | | 0.1 | 108.1 |
| | Composition 18 | | | 40 | | | 0.1 | 106.1 |
| | Composition 19 | 20 | | 40 | | | 0.1 | 106.1 |
| | Composition 20 | 40 | | 15 | | | 0.1 | 106.1 |
| | Composition 21 | 40 | | 15 | | 2 | 0.1 | 107.1 |
| | Composition 22 | | 50 | | | 2 | 0.1 | 107.1 |
| | Composition 23 | | 45 | | | | 0.1 | 105.1 |
| | Composition 24 | 40 | | 5 | | | 0.1 | 105.1 |
| | Composition 25 | 40 | | 5 | | 2 | 0.1 | 107.1 |
| | Composition 26 | 60 | | 20 | | | 0.1 | 105.1 |
| | Composition 27 | 45 | | 15 | | | 0.1 | 105.1 |
| | Composition 28 | | 30 | | | | 0.1 | 105.1 |
| | Composition 29 | | 30 | | | | 0.1 | 105.1 |
| | Composition 30 | 10 | 30 | | | | 0.1 | 105.1 |
| | Composition 31 | 25 | | 25 | 20 | | 0.1 | 105.1 |
| | Composition 32 | 25 | | 30 | | 4 | 0.1 | 109.1 |
| | Composition 33 | 50 | | 50 | | | 0.1 | 105.1 |
| | Composition 34 | 45 | | 24 | | | 0.1 | 105.1 |
| | Composition 35 | 45 | | 24 | | 2 | 0.1 | 107.1 |
| | Composition 36 | 45 | | 40 | | 2 | 0.1 | 107.1 |
| | Composition 37 | 40 | | 30 | | | 0.1 | 105.1 |
| | Composition 32 | | 25 | | | | 0.1 | 105.1 |
| | Composition 39 | | 25 | | | 2 | 0.1 | 107.1 |
| | Composition 40 | | 15 | | | | 0.1 | 105.1 |
| | Composition 41 | 10 | 25 | 20 | | | 0.1 | 100.15 |
| | Composition 42 | 10 | 25 | 20 | | | 0.1 | 122.1 |
| | Composition 43 | 30 | | 40 | | | 0.1 | 105.1 |

TABLE 3-continued

| | | | | |
|---|---|---|---|---|
| Composition 44 | 30 | 40 | 0.1 | 101.1 |
| Composition 45 | 30 | 40 | 0.1 | 110.1 |

Evaluations of an initial adhesive property and an adhesive durability to a resin cured material, and an operability of Compositions 1-42 are shown in Table 4.

TABLE 4

| | Primer composition | Adhesive strength (Mpa) | |
|---|---|---|---|
| | | Initial | Durability |
| Example 1 | Compositon 1 | 25.9 | 26.7 |
| Example 2 | Compositon 2 | 30.4 | 28.4 |
| Example 3 | Compositon 3 | 25.2 | 23.5 |
| Example 4 | Compositon 4 | 28.4 | 25.7 |
| Example 5 | Compositon 5 | 27 | 24.8 |
| Example 6 | Compositon 6 | 26.5 | 24.6 |
| Example 7 | Compositon 7 | 26.3 | 24.2 |
| Example 8 | Compositon 8 | 29.3 | 23.5 |
| Example 9 | Compositon 9 | 30.5 | 28.4 |
| Example 10 | Compositon 10 | 23.6 | 23.2 |
| Example 11 | Compositon 11 | 27.4 | 26.3 |
| Example 12 | Compositon 12 | 28.9 | 27.4 |
| Example 13 | Compositon 13 | 27.7 | 26.9 |
| Example 14 | Compositon 14 | 26.8 | 24.5 |
| Example 15 | Compositon 15 | 31.7 | 25.5 |
| Example 16 | Compositon 16 | 26.8 | 26.4 |
| Example 17 | Compositon 17 | 27.2 | 25.9 |
| Example 18 | Compositon 18 | 26.1 | 95 |
| Example 19 | Compositon 19 | 27.2 | 25.3 |
| Example 20 | Compositon 20 | 28.4 | 26.2 |
| Example 21 | Compositon 21 | 18.5 | 15.2 |
| Example 22 | Compositon 22 | 16.4 | 16.6 |
| Example 23 | Compositon 23 | 18.5 | 14.5 |
| Example 24 | Compositon 24 | 16.3 | 15.2 |
| Example 25 | Compositon 25 | 19.4 | 17.5 |
| Example 26 | Compositon 26 | 16.6 | 14.2 |
| Example 27 | Compositon 27 | 17.7 | 16.1 |
| Example 28 | Compositon 28 | 18.2 | 17.7 |
| Example 29 | Compositon 29 | 15.7 | 13.8 |
| Example 30 | Compositon 30 | 17.2 | 16.9 |
| Comparative Example 1 | Compositon 31 | 4.5 | 0 |
| Example 31 | Compositon 32 | 7.2 | 2.3 |
| Comparative Example 2 | Compositon 33 | 5.5 | 0 |
| Example 32 | Compositon 34 | 6.2 | 5.5 |
| Example 33 | Compositon 35 | 2.9 | 2.9 |
| Example 34 | Compositon 36 | 14.5 | 17.3 |
| Comparative Example 3 | Compositon 37 | 5.5 | 0 |
| Example 35 | Compositon 38 | 12.3 | 6.4 |
| Example 36 | Compositon 39 | 11.4 | 7.2 |
| Example 37 | Compositon 40 | 8.7 | 9.5 |
| Example 38 | Compositon 41 | 2.6 | 2.6 |
| Example 39 | Compositon 42 | 3.5 | 2.8 |
| Example 40 | Compositon 43 | 4.5 | 3.9 |
| Example 41 | Compositon 44 | 6.3 | 5.8 |
| Example 42 | Compositon 45 | 8.7 | 9.1 |

| | Primer composition | Operability | |
|---|---|---|---|
| | | Application property | Air dry ability |
| Example 1 | Compositon 1 | A | A |
| Example 2 | Compositon 2 | A | A |
| Example 3 | Componiton 3 | A | A |
| Example 4 | Compositon 4 | A | A |
| Example 5 | Compositon 5 | A | A |
| Example 6 | Compositon 6 | A | A |
| Example 7 | Compositon 7 | A | A |
| Example 6 | Compositon 8 | A | A |
| Example 9 | Compositon 9 | A | A |
| Example 10 | Compositon 10 | A | A |
| Example 11 | Compositon 11 | A | A |
| Example 12 | Compositon 12 | A | A |
| Example 13 | Compositon 13 | A | A |
| Example 14 | Compositon 14 | A | A |
| Example 15 | Compoziton 15 | A | A |
| Example 16 | Compositon 16 | A | A |
| Example 17 | Compositon 17 | A | A |
| Example 18 | Compositon 18 | A | A |
| Example 19 | Compositon 19 | A | A |
| Example 20 | Compositon 20 | A | A |
| Example 21 | Compositon 21 | A | A |
| Example 22 | Compositon 22 | A | A |
| Example 23 | Compositon 23 | A | A |
| Example 24 | Compositon 24 | A | A |
| Example 25 | Compositon 25 | A | A |
| Example 26 | Compositon 26 | A | A |
| Example 27 | Compositon 27 | A | A |
| Example 28 | Compositon 26 | A | A |
| Example 29 | Compositon 29 | A | A |
| Example 30 | Compositon 30 | A | A |
| Comparative Example 1 | Compositon 31 | A | A |
| Example 31 | Compositon 32 | A | A |
| Comparative Example 2 | Compositon 33 | C | C |
| Example 32 | Compositon 34 | A | A |
| Example 33 | Compositon 35 | A | A |
| Example 34 | Compositon 36 | A | B |
| Comparative Example 3 | Compositon 37 | B | A |
| Example 35 | Compositon 38 | A | A |
| Example 36 | Compositon 39 | A | B |
| Example 37 | Compositon 40 | B | A |
| Example 38 | Compositon 41 | A | A |
| Example 39 | Compositon 42 | B | B |
| Example 40 | Compositon 43 | A | A |
| Example 41 | Compositon 44 | A | A |
| Example 42 | Compositon 45 | B | B |

In each of Examples 1-30 (Compositions 1-30, it was confirmed that one-pack type primer composition exhibits a stable adhesive property to a resin cured article. Especially, Examples 1-30 (Compositions 1-30) including 15.0-30.0 parts by the weight of (A) a polymerizable monomer having a solubility parameter (an SP value) in the range of from 7.0 to 10, 10.0-30.0 parts by the weight of (B) a volatile organic solvent, 4.0-8.0 parts by the weight of (C) a polymerization catalyst and/or a polymerization accelerator and 40.0-75.0 parts by the weight of (D) a polymerizable monomer having at least two polymerizable group, based on 100 parts by weight of a total content of the polymerizable monomer having a solubility parameter (an SP value) in the range of from 7.0 to 10 (A), the volatile organic solvent (B), and the polymerizable monomer having at least two polymerizable group (D), have an extremely high adhesive property and excellent operability.

In Comparative Example 1 including 2-HEMA which has 10.4 of solubility parameter (an SP value) and is more hydrophilic polymerizable monomer than (A) a polymerizable monomer having a solubility parameter (an SP value) in the range of from 7.0 to 10 instead of (A) a polymerizable monomer having a solubility parameter (an SP value) in the range of from 7.0 to 10, it was confirmed that because a wettability to a resin cured material is low, an adhesive durability is poor.

In Example 31 compounded with NMA which has 8.4 of solubility parameter (an SP value) and 121.3 of molecular weight, it was confirmed that because a permeability or an impregnate ability to a resin cured material may decrease, although an adhesive property exhibits, both an initial adhesive property and an adhesive durability are 10 MPa or less.

In Comparative Example 2 which does not include (A) a polymerizable monomer having a solubility parameter (an SP value) in the range of from 7.0 to 10.0 and (B) a volatile organic solvent, it was confirmed that because a permeability or an impregnate ability to a resin cured material is low, an adhesive property does not exhibit. In Examples 32 and 33 with reduced amount of (A) a polymerizable monomer having a solubility parameter (an SP value) in the range of from 7.0 to 10.0, it was confirmed that because a permeability or an impregnate ability to a resin cured material decrease, an adhesive property decrease. In Example 35, it was confirmed that because the content of (A) a polymerizable monomer having a solubility parameter (an SP value) in the range of from 7.0 to 10.0 is too large with respect to the content of (D) a polymerizable monomer having at least two polymerizable group, a polymerizability decrease and an adhesive durability decrease.

In Example 34, it was confirmed that because of including excess amount of (D) a polymerizable monomer having at least two polymerizable group, an operability decrease. In Comparative Example 3, it was confirmed that because (B) a volatile organic solvent is not included, an operability, especially an application property is bad and an adhesive property does not exhibit. In Example 37, it was confirmed that because the content of (D) a polymerizable monomer having at least two polymerizable group decrease, an application property decrease, polymerizability decrease and therefore an adhesive strength is around 9 MPa.

In Example 36, it was confirmed that because of including excess amount of (B) a volatile organic solvent, a removability of solvent decrease, and an air dry ability decrease.

In Examples 38 and 41, it was confirmed that because the content of (C) a polymerization catalyst and/or a polymerization accelerator is excessively low, a polymerizability at an adhesive interface decrease. In Examples 39 and 42, it was confirmed that because the content of (C) a polymerization catalyst and/or a polymerization accelerator is excessively high, an operation surplus time is very short and therefore an operational time is not secured sufficiently, and further polymerization progresses rapidly, therefore stress is concentrated near an adhesive interface, and an adhesive property is decrease.

In Example 40, it was confirmed that because an aromatic amine is not compounded, a curability at an adhesive interface decrease and an adhesive strength is around 4 MPa.

[Method of Preparing Two-Pack Type Primer Composition]

Two-packs type primer compositions consisting of primer A and B were prepared by loading materials shown in Table 5 into a container under light shielding, and then the materials were stirring and mixing by Turbula mixer (T2F: manufactured by Shinmaru Enterprises Corp.) for 24 hours, and confirming that the resultant is in a dissolved state.

TABLE 5

| | Primer A | | | | | | | | | |
|---|---|---|---|---|---|---|---|---|---|---|
| | (A) a polymerizable monomer having a solubility parameter (an SP value) in the range of from 7.0 to 10.0 | | | (B) a volatile organic solvent | | (C) a polymerization catalyst and/or a polymerization accelerator | | | | |
| | MAA | MMA | BAA | Aceton | EtOH | DMPT | DEPT | CQ | APO | DMBE | pTNa |
| SP value | 9 | 8.2 | 8.8 | — | — | — | — | — | — | — | — |
| Molecular weight (g/mol) | 86 | 100.1 | 128.2 | — | — | — | — | — | — | — | — |
| Composition 46 | 20 | | | 20 | | | 2 | 1 | | 1 | |
| Composition 47 | | 25 | | 10 | | 2 | | | 1 | | 1 |
| Composition 48 | | | 30 | | 25 | | 4 | 1 | | 1 | |

| | Primer B | | | | | | |
|---|---|---|---|---|---|---|---|
| | (D) a polymerizable monomer having at least two polymerizable group | | | (C) a polymerization catalyst and/or a polymerization accelerator | Other component additives etc. | | |
| | UDMA | Bis-GMA | TEGDMA | BPO | R-7200 | BHT | Total |
| SP value | 10.5 | 11 | 9 | — | — | — | — |
| Molecular weight (g/mol) | 470.6 | 512.6 | 286.3 | — | — | — | — |
| Composition 46 | 45 | 15 | | | 1 | 0.1 | 105.1 |
| Composition 47 | 40 | 25 | | | | 0.1 | 104.1 |
| Composition 48 | 25 | 20 | | 2 | | 0.1 | 108.1 |

Evaluations of an initial adhesive property and an adhesive durability to a resin cured material and an operability in Compositions 46-48 are shown in Table 6.

TABLE 6

| Primer composition | Adhesive strength (Mpa) | | Operability | |
|---|---|---|---|---|
| | Initial | Durability | Application property | Air dry ability |
| Example 43 Composition 46 | 35.5 | 34.2 | A | A |
| Example 44 Composition 47 | 34.2 | 38.5 | A | A |
| Example 45 Composition 48 | 35.1 | 32.7 | A | A |

In each of Examples 43-45 (Compositions 46-48), it was confirmed that two-packs type primer composition has a satisfactory adhesive property to a resin cured article and operability

TABLE 7

| Polymerizable monomer | Structure | SP value | Molecular weight |
|---|---|---|---|
| MMA; Methyl methacrylate | 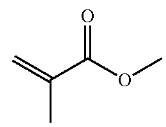 | 8.2 | 100.12 |
| MAA; Methyl acrylate | 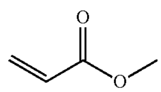 | 9.0 | 86.04 |
| EMA; Ethyl methacrylate | 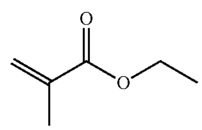 | 8.3 | 114.14 |
| EAA; Ethyl acrylate | 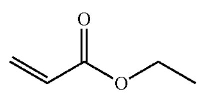 | 8.9 | 100.12 |
| BAA; Butyl acrylate | 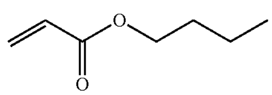 | 8.8 | 128.17 |
| BMA; Butyl methacrylate | 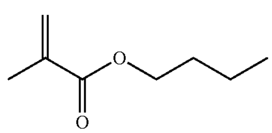 | 8.3 | 142.2 |
| HMA; Hexyl acrylate | 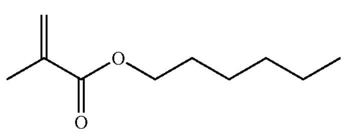 | 8.4 | 170.25 |
| 2-hydroxypropyl acrylate | 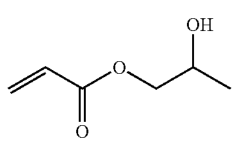 | 11.0 | 130.14 |
| 2-HEMA; 2-hydroxyethyl methacrylate | 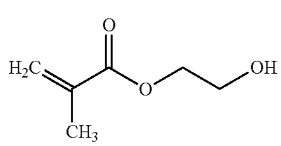 | 11.5 | 130.14 |
| 2-HEAA; 2-hydroxy-ethylacrylate | 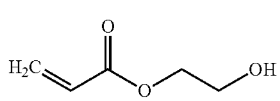 | 10.4 | 116.12 |

TABLE 7-continued

| Polymerizable monomer | Structure | SP value | Molecular weight |
|---|---|---|---|
| EM-1; Ethylene glycol dimethacrylate | 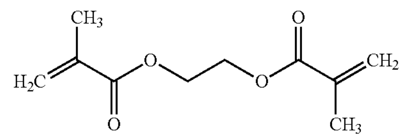 | 8.9 | 198.22 |
| GDMA; Glycerol dimethacrylate | 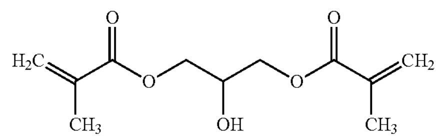 [SMILES: C=C(C)C(=O)OCC(O)COC(=O)C(=C)C] | 10.1 | 228.24 |
| NMA; Nonyl methacrylate | 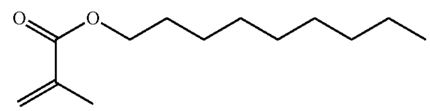 | 9.1 | 212.33 |
| Bis-GMA | 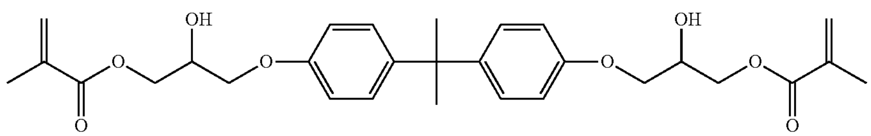 [SMILES: C=C(C)C(=O)OCC(O)COc1ccc(C(C)(C)c2ccc(OCC(O)COC(=O)C(=C)C)cc2)cc1] | 11.0 | — |
| UDMA | 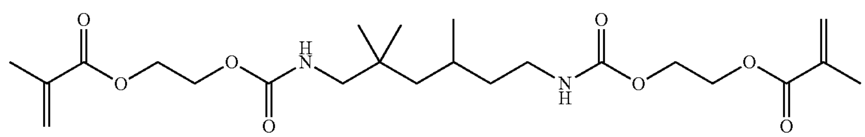 [SMILES: C=C(C)C(=O)OCCOC(=O)NCCC(C)CC(C)(C)CNC(=O)OCCOC(=O)C(=C)C] | 10.5 | — |
| TEGDMA | 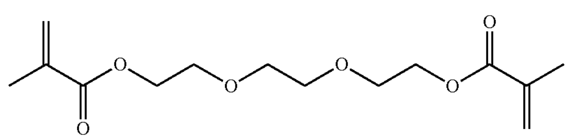 [SMILES: C=C(C)C(=O)OCCOCCOCCOC(=O)C(=C)C] | 9.0 | — |

What is claimed is:

1. A primer composition for a resin cured material, comprising:
    (A) a polymerizable monomer having a solubility parameter (an SP value) in the range of from 7.0 to 10.0,
    (B) a volatile organic solvent,
    (C) a polymerization catalyst and/or a polymerization accelerator comprising at least one selected from the group consisting of N,N-dimethyl-p-toluidine and N,N-di(2-hydroxyethyl)-p-toluidine, and
    (D) a polymerizable monomer having at least two polymerizable group,
    wherein a content of the polymerization catalyst and/or the polymerization accelerator (C) is 4.0 to 8.0 parts by weight, based on 100 parts by weight of a total content of the polymerizable monomer (A), the volatile organic solvent (B), and the polymerizable monomer (D).

2. The primer composition for a resin cured material according to claim 1, wherein:
    a molecular weight of the polymerizable monomer having a solubility parameter (an SP value) in the range of from 7.0 to 10.0 (A) is 150 or less.

3. The primer composition for a resin cured material according to claim 1, wherein:
    a content of the polymerizable monomer having a solubility parameter (an SP value) in the range of from 7.0 to 10.0 (A) is 5.0 to 60.0 parts by weight based on 100 parts by weight of a total content of the polymerizable monomer (A), the volatile organic solvent (B), and the polymerizable monomer (D).

4. The primer composition for a resin cured material according to claim 1, wherein:
    an aromatic amine is compounded as the polymerization catalyst and/or a polymerization accelerator (C).

5. The primer composition for a resin cured material according to claim 2, wherein:
    a content of the polymerizable monomer having a solubility parameter (an SP value) in the range of from 7.0 to 10.0 (A) is 5.0 to 60.0 parts by weight based on 100 parts by weight of a total content of the polymerizable monomer (A), the volatile organic solvent (B), and the polymerizable monomer (D).

6. The primer composition for a resin cured material according to claim 2, wherein:
    an aromatic amine is compounded as the polymerization catalyst and/or a polymerization accelerator (C).

7. The primer composition for a resin cured material according to claim 3, wherein:
    an aromatic amine is compounded as the polymerization catalyst and/or a polymerization accelerator (C).

* * * * *